(12) United States Patent
Hammerstedt et al.

(10) Patent No.: US 7,407,796 B2
(45) Date of Patent: Aug. 5, 2008

(54) INTERROGATION OF CHANGES IN THE CONTENTS OF A SEALED CONTAINER

(75) Inventors: Roy H. Hammerstedt, Boalsburg, PA (US); Allen T. Phillips, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 10/840,178

(22) Filed: May 6, 2004

(65) Prior Publication Data

US 2004/0206658 A1 Oct. 21, 2004

Related U.S. Application Data

(63) Continuation of application No. 09/772,272, filed on Jan. 29, 2001, now abandoned.

(60) Provisional application No. 60/179,164, filed on Jan. 31, 2000.

(51) Int. Cl.
*C12M 1/34* (2006.01)

(52) U.S. Cl. ............... 435/287.2; 422/82.05; 422/82.08; 435/7.2; 435/7.32; 435/288.5; 435/288.7; 435/808; 436/164; 436/172; 436/518; 436/524; 436/528; 436/530; 436/805

(58) Field of Classification Search ............... 435/287.4, 435/287.6, 287.7, 287.8, 287.9, 288.7
See application file for complete search history.

(56) References Cited

U.S. PATENT DOCUMENTS

| | | | |
|---|---|---|---|
| 4,200,110 A | 4/1980 | Peterson et al. | |
| 4,513,607 A | 4/1985 | Coupal | |
| 4,666,672 A | 5/1987 | Miller et al. | |
| 4,743,629 A | 5/1988 | Karakelle et al. | |
| 4,785,814 A | 11/1988 | Kane | |
| 4,816,130 A | 3/1989 | Karakelle et al. | |
| 4,978,503 A | 12/1990 | Shanks et al. | |
| 5,114,864 A * | 5/1992 | Walt ........................... | 436/528 |
| 5,164,796 A * | 11/1992 | Di Guiseppi et al. ......... | 356/445 |
| 5,194,393 A * | 3/1993 | Hugl et al. .................. | 436/525 |
| 5,261,870 A | 11/1993 | Hammerstedt et al. | |
| 5,408,999 A | 4/1995 | Singh et al. | |
| 5,605,809 A | 2/1997 | Komoriya et al. | |
| 5,814,449 A * | 9/1998 | Schultz et al. ................. | 435/6 |
| 5,976,827 A * | 11/1999 | Jeffrey et al. ................. | 435/34 |
| 6,210,910 B1 | 4/2001 | Walt et al. | |
| 6,266,459 B1 | 7/2001 | Walt et al. | |
| 6,315,767 B1 | 11/2001 | Dumont et al. | |
| 6,377,721 B1 | 4/2002 | Walt et al. | |
| 6,558,546 B2 | 5/2003 | Allcock et al. | |
| 6,667,159 B1 | 12/2003 | Walt et al. | |
| 6,726,671 B2 | 4/2004 | Dumont et al. | |
| 6,790,672 B2 | 9/2004 | Balkus, Jr. et al. | |
| 6,859,570 B2 | 2/2005 | Walt et al. | |

* cited by examiner

*Primary Examiner*—Christopher L Chin
(74) *Attorney, Agent, or Firm*—The Webb Law Firm

(57) ABSTRACT

A device and method allowing evaluation of the contents of a sealed primary container by means of an integral sensor which is separated from the contents of the sealed primary container yet provides information on quality of the contents of the primary container without breaking the sealed system. The integral sensor device includes a biosensor retained within a plastic construct by a gated-pore membrane. Pores in the membrane open in response to an environmental change in the primary container allowing the contents of the primary container to contact the biosensor. Status of the contents of the primary container can be determined by inspection of the biosensor, visually or via a fiberoptic probe, through the optical window of the plastic construct.

13 Claims, 13 Drawing Sheets

INTERROGATION OF CHANGES IN THE CONTENTS OF A SEALED CONTAINER

RELATED APPLICATION

This application is based on priority Provisional Application Ser. No. 60/179,164, filed Jan. 31, 2000.

BACKGROUND OF THE INVENTION

1. Field of the Invention

This invention relates to analyte enclosures to be used in conjunction with sensing devices. In particular, this invention relates to evaluation of the contents of a sealed primary container by means of an integral sensor which is separated from the contents of the sealed primary container yet provides information on quality of the contents of the primary container without breaking the sealed system.

2. Description of the Related Art

The background for this invention is presented in the context of human blood cells, because of their great societal importance and especially because of limitations of current procedures used for their storage. However, the invention could have been presented in a context of food storage and processing, production of valuable molecules by biofermentation, or industrial processing such as electroplating or acid/base treatment of products.

Typically, blood is obtained from donors and fractionated into components including erythrocytes, platelets, lymphocytes, and plasma. Erythrocytes and platelets are separately packaged as "units", which then are held at appropriate temperature and distributed for later transfusion into patients. Each unit is aseptically placed into a previously sterilized plastic bag and sealed therein. Despite careful attention to aseptic processing, there is a probability that a given unit of blood cells will be contaminated with microbes.

With erythrocytes, current FDA regulations limit use to within 24 days after collection in an effort to minimize risk to patients from infusion of a contaminated unit of cells. Often endotoxins rather than the bacteria per se cause the problem with erythrocytes. With platelets, there is similar concern about microbial contamination, but their use is limited to 5 days because of metabolic self-damage. A recent review (Blajchmann, 1999) noted that 1 in ~2,500 units of platelets and 1 in ~38,500 units of erythrocytes was contaminated with bacteria. A New Zealand study reported that 1 of 65,000 individuals will get very sick after transfusion of erythrocytes and 1 of 104,000 will die because of one specific organism. Data from other countries, including the USA, provide both higher and lower risk factors, but there is substantial hazard associated with use of erythrocytes and especially platelets (Lee, 1999).

Currently there is no acceptable method to determine if a unit of blood is contaminated just before transfusion of the contents into a patient. This is because sampling the contents requires opening the bag, with resultant risk of introducing contamination, and evaluation of the sample acquired. Because a laboratory setting is required, it is difficult or impossible to make a "use" or "non-use" decision in a few minutes. Clearly, a diagnostic method or device to allow a use or non-use decision without opening the unit of blood would have great utility if it had a very high probability of giving the correct conclusion.

BRIEF DESCRIPTION OF THE INVENTION

A device and method of the present invention allows evaluation of the contents of a sealed primary container by means of an integral sensor which is separated from the contents of the sealed primary container yet provides information on quality of the contents of the primary container without breaking the sealed system. The integral sensor device includes a biosensor retained within a plastic construct by a gated-pore membrane. Pores in the membrane open in response to an environmental change in the primary container allowing the contents of the primary container to contact the biosensor. Status of the contents of the primary container can be determined by inspection of the biosensor, visually or via a fiber-optic probe, through the optical window of the plastic construct.

DETAILED DESCRIPTION OF THE INVENTION

Figure 1:
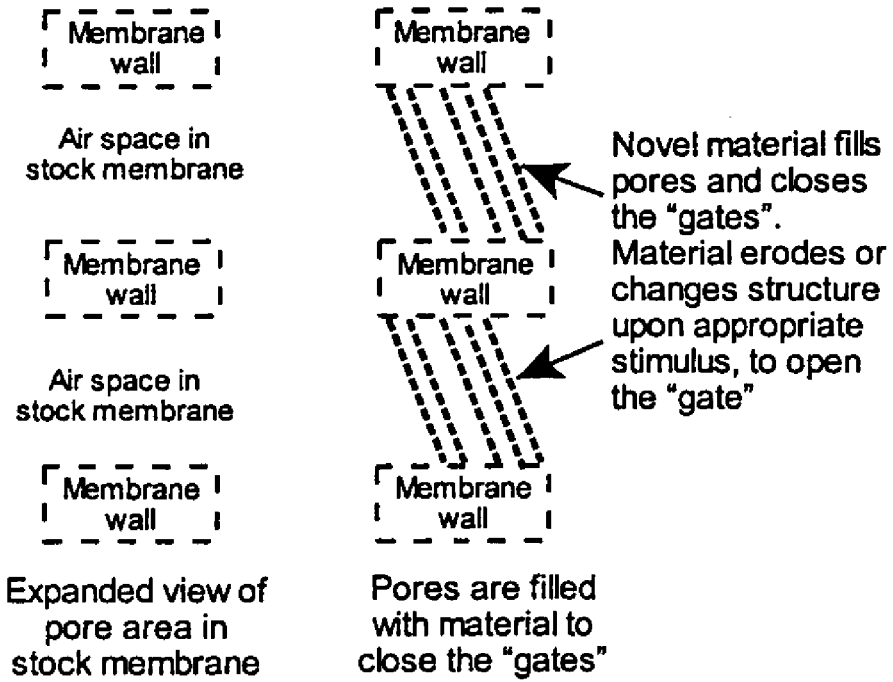
FIG. 1 is a schematic representation of a stock membrane and an occluded membrane according to the present invention.

Primary container—In this disclosure, we use the term "primary container" in a broad sense, to include any container for cells, foods, or industrial materials.

Integral sensor—In this disclosure, we use the term "integral sensor" to designate one of many devices as disclosed herein. An "integral sensor" typically is incorporated into a primary container, prior to sterilization if appropriate, and separates a biosensor (see below) from the contents of the sealed primary container yet provides information on quality of the contents of the container without breaking the sealed system.

Gated-pore membrane—In this disclosure, we use the term "gated-pore membrane" in a broad sense, to include any separation barrier containing one or more pores which have been occluded as taught in U.S. Pat. No. 5,261,870, pending patents, or other procedures. Such a separation barrier has one or more pores which initially are closed, but which will open in response to a change in the local environment to an extent sufficient to allow passage of ions or molecules, as appropriate. The occluding material might erode, dissolve, or change three-dimensional form, depending on design of the gated-pore membrane.

Gate—In this disclosure, we use the term "gate" in reference to one or more pores through a separation barrier. The gate is "closed" if the pore is occluded to prevent passage of ions or molecules. The gate is "open" if the occluding material has eroded, dissolved or changed three-dimensional form sufficiently to allow passage of one or more species of selected ions or molecules.

Sensor compartment—In this disclosure, we use the term "sensor compartment" in reference to a component of an integral sensor, with said component formed in part from a gated-pore membrane and in part from a plastic construct. The sensor compartment contains and positions a biosensor where it can become accessable to ions, molecules, or cells entering from the primary container and also positions that biosensor where it can be interrogated in a consistent manner through a special optical window or, alternatively, through a portion of the primary container.

Biosensor—In this disclosure, we use the term "biosensor" in reference to a component of a device, with said component designed to respond to a molecular change(s) in the local environment in a known and consistent manner with a response or signal that can be detected or measured using procedures known to those skilled in the art. The change in local environment, or microenvironment, might be ionic, molecular or cellular in nature.

Receptor—In this disclosure, we use the term "receptor" in reference to any detector molecule, either synthetic or natural in origin, or antibody incorporated into a biosensor. A receptor has reasonable affinity and specificity for one or more "ligands" (see below).

Ligand—In this disclosure, we use the term "ligand" in reference to a specific ion(s), molecule(s), or cell(s) accumulating or disappearing within a primary container over time. Accumulation of ligand within the primary container will result in a change in the proportion of unoccupied receptor to ligand-receptor complexes, and a change in characteristics the of a biosensor.

The present invention consists of devices and methods which allow evaluation of the contents of a sealed primary container by means of an integral sensor which is separated from the contents of the sealed primary container yet provides information on quality of the contents of the primary container without breaking the sealed system. The integral sensor device might be a hollow cylinder or a shallow construct. One end or face of the device is a gated-pore membrane whose pores normally are occluded, by one of many approaches, forming one end of a sensor compartment, containing a biosensor appropriate for the task, with the other end of the sensor compartment formed by an optical window recessed in from the end opposite to the gated-pore membrane or formed by a wall of the primary container. Typically, the integral sensor device is fabricated separately from the primary container and incorporated into the primary container during final fabrication, before sterilization. Certain embodiments of the device are therefore capable of aseptic operation. The status of the contents of a primary container for blood cells, other cells, foods, or industrial products can be determined by inspection, visually or via a fiber-optic probe through the optical window of a plastic construct incorporated into said primary container at fabrication, of the biosensor retained within said plastic construct by a gated-pore membrane, the pores in which opened in response to an environmental change in said primary container allowing the contents of said primary container to contact and cause a change in said biosensor. In one embodiment, after the cell suspension or product is placed into the container, the gated-pore membrane opens and allows continuous exposure of the biosensor, within the sensor compartment, to the contents of the primary container. Changes within the primary container affect the signal from the biosensor, which can be quantified at any instant in time by viewing the optical window of the device with an appropriate sensor, as above, providing a measure of quality without opening the primary container. In another embodiment, after the cell suspension or product is placed into the container, the gated-pore membrane remains closed until a predetermined change occurs within the primary container which causes the gated-pore membrane to open allowing fluid to enter the sensor compartment and contact the biosensor, which then responds with an appropriate signal. Changes in the primary container that can be detected include, but are not limited to, a decrease or increase in pH away from a threshold value or accumulation of one or more members of a preselected class of molecules, including toxins produced by bacteria, above a threshold value. A great range in utility is possible because, depending on the device and method, both the material(s) occluding the gated-pore membrane and material(s) forming the biosensor can be varied independently or in combination. Hence, a predetermined change in contents of the primary container can be evidenced by opening of the gated-pore membrane and/or a change in the signal from the biosensor. A number of other embodiments or uses would be obvious to one skilled in the art, and the examples herein illustrate but do not set the limits of this invention.

An ideal test should detect one bacterium in the presence of 10,000 platelets, with a low false positive (contaminated) rate, and be reliable regardless of the species of contaminant, simple in complexity, completed in minutes, and low in cost. This might be unattainable, but can be approached by combining emerging technologies in a novel manner. For example, it is known that bacteria can be collected on surfaces using synthetic materials (Hogt et al., 1983; Mackenzie and Rivera-Calderon, 1985; Barrett, 1988; Barth et al., 1989) or biomaterials (Abraham, et al., 1983; Kuusela et al., 1985; Vercellotti et al., 1985; Speziale et al., 1986; Herrmann et al., 1988). Incorporation of such materials into a gated-pore membrane or biosensor, as disclosed herein, should enhance the probability of detecting such organisms.

Conventional membranes with pores of known size (e.g., 0.1 or 3.0 m nominal diameter) can be fabricated into special gated-pore membranes, and then fabricated into a container or other device (U.S. Pat. No. 5,261,870). The gated-pore membrane can provide a closed container which opens only when predefined conditions are met, and the material occluding or otherwise closing the pores is altered so that the gates previously blocking passage of molecules through the pores is opened. An almost infinite combination of membranes, pore diameters, and occluding materials is envisioned in U.S. Pat. No. 5,261,870 and other disclosures. Importantly, the conditions on one side of the gated-pore membrane and not mechanical, electrical or other interventions, determine when the pores open and allow passage of molecules through the membrane into the sensor compartment.

Biosensors can be designed to respond to many molecular changes in the environment. The color change of a pH indicator in response to proton concentration or certain dipsticks to glucose concentration are two common and simple examples. Biosensors sensitive to one or another molecular stimulus can be incorporated into beads or micro-beads, and frequently can be designed to change color or emit light of a given wavelength when exposed to light of an appropriate wavelength (i.e., fluorescence). These or other changes can be monitored with a variety of detectors, ranging from the human eye to fiberoptic electronic devices with a digital readout.

Obviously, if a gated-pore membrane, with appropriate properties, served to seal an appropriate biosensor within an otherwise impervious container, the gated-pore membrane would: (a) retain the biosensor in place; and (b) determine when, if ever, the biosensor received the stimulus driving the response. Such a device could be a plastic cylinder, series of concentric cylinders, shallow construct, or of any other shape so long as it positioned the biosensor in a manner conveniently accessible to the detection device. If desirable, the device might include a clear optical window, through which a separate detector could view the biosensor, but would have opaque walls to minimize stray light from falling on the sensor or detector. Although not necessary, frequently, it would be desirable to have the optical window, and the sensor compartment, located more than 1 cm from the open end of the construct (the end opposite from that with the gated-pore membrane). Alternatively, a portion of the wall of the primary container can serve as the optical window to view a biosensor contained in a shallow construct.

In one embodiment, the gated-pore membrane is fabricated using an occluding polymer such as methylcellulose, or other polymers or mixtures taught in U.S. Pat. No. 5,261,870 with the intent that the pores would remain occluded until a cell suspension had been placed into the primary container incorporating the device. At a predetermined interval (e.g., 5 to 15 minutes) after water contacted the gated-pore membrane, the occluding material would erode or dissolve, the gates open, and free exchange of molecules across the membrane would occur by diffusion and other forces. The biosensor then would start to sample the contents of the primary container, limited only by diffusion within the sensor compartment, diffusion across the gated-pore membrane, and correctness of the sampling site of the external face of the gated-pore membrane. Occasional or continuous movement of the primary container or its contents might facilitate accurate sampling. Changes in the biosensor might be detected visually or via a fiberoptic probe and appropriate instrumentation. In this embodiment, the biosensor provides specificity for detection of molecular changes within the primary container, and the gated-pore membrane retains the biosensor and prevents premature sampling.

In another embodiment, the gated-pore membrane is fabricated with a special occluding material selected to respond to a specific stimulus and not the mere presence of water. An incomplete list of materials which might be used to occlude the pores in membranes used for this embodiment is provided below. This stimulus opening the gated-pores might be a decline in pH within the primary container, possibly caused by normal cellular metabolism or especially that of contaminating microbes, or accumulation of a secreted bacterial toxin. In this embodiment, the gated-pore membrane remains closed after the cell suspension or product is placed into the container and opens only if and when the triggering stimulus occurs. At that time, the gated-pores open allowing water to pass through the membrane and into the detector compartment, carrying along whatever ions or molecules that might be in the water. The sensor would change from contact with water, for example from a green to a white color discernable by the human eye, or in response to specific molecules or ions entering the detector chamber with the water. In the case of a simple color change in such a pH-sensitive device incorporated into a bag of erythrocytes, visual inspection for a green rather than a white color before use might be sufficient to preclude a decreased pH associated with microbial contamination.

In these or other embodiments, it is not essential that the material occluding the gated-pore membrane completely block the pores or micropores through the membrane, so long as the molecules to which the biosensor responds cannot gain access through the membrane to the biosensor.

Utility of such devices is defined by the combination of membrane stock plus materials plugging the pores to form the gated-pore membrane, precision or repeatability in opening of the occluded pores, nature of the biosensor, and sensitivity of the detector plus biosensor to detect the monitored event. Depending on the application, the magnitude of the change to trigger a detected response can be adjusted either via the occluding material or the biosensor. In all cases, response of the detector is not dependent on mechanical or electrical forces, although readout might require an instrument. With appropriate instrumentation, signals in a remote or isolated area can be detected.

Membrane Stock Materials

Membrane stock used to form the gated-pore membrane can be any of those commercially available, e.g., fibril membranes with a "haystack" structure, microporous membranes with a "sponge-like" structure, and track-etched or capillary-pore membranes with a "tunnel" structure. Although others have used membranes, either preformed or formed in place, to position biosensors against a fiberoptic or other detector, gated-pore membranes have not been used for this purpose. Gated-pore membranes for this application could be prepared using microporous membrane stock. However, characteristics unique to capillary-pore membrane stock frequently make this the material of choice to form gated-pore membranes for use in biosensor detectors as described herein. Alternatively, one might use a stock membrane which incorporates the ability to change in response to pH (Maeda et al., 1984; Kinoshita et al., 1994).

Materials to Occlude Pores in Membrane Stock

Materials to occlude preformed pores in a stock membrane and, thereby, form a gated-pore membrane, might be selected from members of the classes listed below, but these are illustrative and not inclusive. A generic resultant gated-pore membrane is illustrated in FIG. 1. Importantly, occluding material within the pores is the functional element rather than residual occluding material that might be retained on the membrane faces around the pores. Many of the potentially useful materials have been used for other applications, but none has been used to fill preformed pores in a membrane to control access of material on one side of the membrane to a biosensor positioned behind the membrane where accessible to a detector. All materials applicable for this application are considered as under the scope of this invention, recognizing that in some instances the material might be patented.

1. Non-protein polymers responding to changes in pH by dissolution or a change in hydration and volume such as carboxymethyl or diethylamino cellulose. When used to occlude pores in conventional membrane stock, such polymers shrink (open the "gate") in response to pH.
2. Protein polymers responding to changes in pH or other environmental factor(s), by a change in conformation or other attributes. Such proteins become longer or shorter, or greater or lesser in globular vs. linear or helical nature, in response to pH (Ito et al., 1990, 1997; Huyghues- Despointes et al., 1993; Holtzer, 1994; Spek et al., 1995; Urry, 1997) and thus open or close the "gates".

3. Lipid bilayers or similar lipid-containing composites responding to an increased concentration of a bacterial product, such as a secreted toxin (e.g., porin-type toxins secreted by *E coli, Staphyloccus,* or *Streptococus*). Numerous methods might be used to prepare lipid bilayers (U.S. Pat. No. 5,368,712; Sackmann, 1996) supported by the structure of tunnels within a capillary-pore membrane.

Materials to Form or Coat Biosensors

Understanding of a biosensor is facilitated by analogy to classic receptor-ligand interactions, where in respect to this invention the term "receptor" is any detector molecule, either synthetic or natural in origin, or antibody bound on a solid substrate, termed the biosensor, and the term "ligand" is a specific ion(s), molecule(s), or cell(s) accumulating or disappearing within a primary container over time. The receptor has reasonable affinity and specificity for the ligand. Accumulation of ligand within the primary container will result in a change in the proportion of unoccupied receptor to ligand-receptor complexes. Appropriate selection of the ligand and receptor molecules allows detection of this change in ratio of unoccupied vs. occupied receptors by an altered spectroscopic property from either of the separate ligand or receptor molecules or their complexes. Alternatively, a signal moiety might be conjugated to the receptor and provide amplified evidence of the status as unoccupied or occupied. If appropriate, the change in ratio of unoccupied vs occupied receptors might be amplified by a property intrinsic to the solid substrate.

There is no limit to biosensors appropriate for this device, insofar as they undergo a change in signal character, upon exposure to the change in microenvironment to be detected, which can be detected or measured by any form of spectroscopy (e.g., luminescence, fluorescence, absorbance, infrared, magnetic, light scatter, etc.). In certain cases, the material or cells stored can provide the requisite signal. However, use of special biosensors increases the nature of changes that can be monitored. Many of the potentially useful biosensors have been used for other applications, but none has been positioned in a viewable compartment formed in part by a gated-pore membrane initiating access of the molecules, ions or bacteria to be detected and formed in part by an optical window allowing detection of the signal resulting from the biosensor. Biosensors often contain two active elements; namely, the detector material(s) and the signal material(s), which frequently are combined within a combination molecule.

Although we use plastic beads as the example solid substrate, this invention is not limited in this respect. The solid substrate can have any three-dimensional shape; include impervious or permeable materials; include smooth, microporous or complex surfaces; etc. This patent is not limited by the nature or shape of the solid substrate. Similarly, this invention is not limited by the method used to attach the detector molecules to the solid substrate.

Detector molecules can be attached to the surface of the biosensor (e.g., plastic or glass bead) by simple adsorption, direct covalent attachment, or via an affinity tag (Anonymous 1999a, 1999b; Nolan et al., 1999; Song and Swanson, 1999). Alternatively, the solid surface might be pre-coated with lipids and then lipophilic ligand-detector molecules partitioned therein (Nolan et al., 1999). If not in a combination molecule with the detector material, the signal material must respond to the change in status of the detector material (occupied vs unoccupied) and the change in the signal must be a change in a characteristic absorption or emission property within the electromagnetic spectrum. An absorbance or fluorescent signal is most common.

Any biosensor appropriate for this application is considered as under the scope of this invention, recognizing that in some instances the biosensor might be patented. In this discussion we will consider a bead-shaped biosensor, but all shapes are claimed. Appropriate concepts for biosensors might be considered in several classes (shown schematically in FIG. 2; for easy reference, given designations herein) which include, but are not limited to:

Class-1: A bead coated with a fluorescent receptor targeting an epitope or ligand characteristic of, or secreted by, bacteria of interest and which fluoresces only when its conformation is altered by binding of the ligand. Detection of bound ligand is via fluorescence when the biosensor is illuminated with light of an appropriate wavelength.

Class-2: A bead coated with lipid in which are positioned appropriate fluorochrome-receptor complexes, anchored therein, which fluoresce only when their conformation is altered by binding of the ligand. Detection of bound bacterial products is via fluorescence when the biosensor is illuminated with light of an appropriate wavelength.

Class-3: A bead coated with lipid or otherwise prepared in which are positioned low concentrations of two different fluorescent receptors each binding the ligand, so that concurrent binding of a ligand molecule by both receptors brings them in closer proximity and enables charge-coupling excitation to produce light of a unique wavelength when the biosensor is illuminated with light of an appropriate wavelength. In this case, appropriate external excitation causes only one receptor to fluoresce and although that light is not detected it does excite, by fluorescence resonance transfer, the second receptor and causes it to emit light of a unique wavelength detectable by the fiberoptic probe. Because fluorescence of the second receptor is dependent on proximity to the first, achieved only by both binding to ligand, such systems can be very specific.

Class-4: A bead coated with lipid or otherwise prepared to accept a mixed-matrix, in which one receptor-A is designed to bind a certain class or type of cell, which after binding continues to release material serving as the ligand bound by the nearby second receptor-B, causing a rapid shift from unoccupied to occupied receptor-B molecules and a detectable spectral change. Positioning a chemoattractant on the biosensor could further enhance sensitivity of a mixed-matrix surface.

Class-5: A bead coated with lipid or otherwise prepared to accept a detection substrate-fluorochrome which can serve as a substrate for a specific class of enzymes secreted by bacteria or other cells. In this biosensor, the substrate is designed to contain two fluorescent groups with one on either side of the enzymatic cleavage site in close proximity while the molecule is intact but substantially farther apart after the substrate is cleaved. Local action of the enzyme on the substrate releases the fluorescent inhibition caused by close proximity, and the detector molecule will fluoresce when illuminated with light of an appropriate wavelength. Bark and Kahn (2000) provided examples.

Class-6: A bead coated with a mixed matrix combining elements of Class-4 and Class-5. As in Class-4, receptor-A binds the cell of interest, without or with help from a chemoattractant, so that the cell continues to release an enzyme in close proximity to a substrate incorporating the fluorescent reporter B-C, as in Class-5. The enzyme from the localized cell (e.g., a bacterium) acts on the substrate and this releases the fluorescent inhibition caused by close proximity, so that the detector molecule will fluoresce when illuminated with light of an appropriate wavelength.

Detection of Signal Emanating from a Biosensor

Assuming incorporation of a fluorescent moiety (e.g., a fluorescent-protein biosensor; Giuliano and Taylor, 1998), flow cytometry is common (microsphere analyte analysis; Morgan et al., 1996; McHugh, 1994; Nolan et al., 1999; Anonymous 1999c, 1999d). Flow cytometry of biosensors has been used to quantify protease, phospholipid antibodies, and water-soluble toxins (St. Piere et al., 1996; U.S. Pat. No. 5,605,809; Laakel et al., 1996; Song et al., 1998). Other materials have been analyzed in solution, but could be used in a solid-phase assay (e.g., zinc and related cations or nucleic acids; Goodwin and Berg, 1996; Tyagi and Kramer, 1996). The other common approach to interrogate the biosensor is via a fiberoptic probe (various shapes, including microspheres; as above).

Detection of a change intrinsic to the contents of a container or via a special biosensor (e.g., with a fluorescent reporter) requires an optical probe (Maroze et al., 1999), either an integral and fixed fiberoptic probe or a separate and removable fiberoptic probe. A fiberoptic probe integral to the container to be analyzed might read an inherent spectral property of materials within the bag. Alternatively, an integral fiberoptic probe might indirectly monitor changes in internal contents via reading a change in an optical property of a biosensor element when the material of interest reaches an appropriate concentration in the immediate environment of the biosensor.

In known devices, the biosensor is immobilized by covalent bonding to the face of the fiberoptic bundle or the biosensor is restrained close to the fiberoptic bundle with a perm-selective membrane. Such systems have been used to monitor anions, cations, biomass, glucose, lactic acid, NAD(P)H, $O_2$, $CO_2$ and pH (Agayn and Walt, 1993; Kar and Arnold, 1995; Marose et al., 1998; Spichiger-Keller, 1997; Tartakovsky et al., 1996; Urbano et al., 1984; Vaccari et al., 1994; Weigl et al., 1994; Xu et al., 1998). These approaches cannot be used with a closed container.

Hitherto, the only option for a closed container was to position a removable fiberoptic probe against an optical window in the primary container to gather information from the materials within the container. However, information gathering has been limited to spectral properties inherent to the materials within the container (e.g., light scatter from biomass, fluorescent properties of metabolites such as NAD(P)H; Cavinato, et al., 1990).

A device to interrogate changes in a closed primary container logically might include an immobilized biosensor, sampling a specific attribute of the contents of said closed primary container, with said biosensor protected in a separate closed sub-container within said device, with said biosensor retained in front of an optical window, with said optical window accessible to a removable fiberoptic detector without opening either said primary container or said sub-container, and with said device capable of facile incorporation into said primary container at the time of manufacture before sterilization. Solution of this hitherto unattainable goal is the subject of this invention. This is achieved by combination of existing technology on gated-pore membranes; bioactive polymers, proteins or lipid films; and biosensors in a novel manner and adding flexibility offered by new materials and configurations in novel devices. Clearly, several elements are combined in a novel manner to provide such devices.

In addition to the devices disclosed herein, uses of the functional elements within the described devices differ from uses in the prior art in several ways. Uses disclosed herein are not obvious extensions of the prior art.

These novel elements include:

1. In respect to bioactive non-protein or protein-polymers used to occlude pores and form a gated-pore membrane, the prior art does not teach the use of:
   (a) a bioactive material bound uniformly and primarily to the interior of tunnels of uniform diameter within a preformed membrane to provide a membrane completely blocking fluid flow until the membrane is exposed to the selected altered environment, after which flow rates for water, molecules or ions are similar to those through the raw membrane stock; or
   (b) black-lipid bilayers to occlude pores in a preformed membrane with the intent of forming gated-pores, opening after exposing the membrane to an appropriate environmental stimulus including such as bacterial toxins.

2. In respect to uses of biosensors, the prior art does not teach a method to position biosensors within a closed primary container in a manner where, after a pre-selected event, they can monitor and display changes within the primary container for repeated interrogation with a separate detector.

3. In respect to receptor-signal molecules of the biosensor, the prior art does not teach the use of:
   (a) pH-sensitive fluorescent complexes formed by attaching a fluorescein-dextran conjugate to carboxyl groups on a bead to provide a Class-1 receptor, allowing repeated measurements of pH by appropriate excitation and detection;
   (b) fluorescent receptor binding α-hemolysin, or other molecule, which changes conformation from non-fluorescent to fluorescent upon occupancy to provide a Class-2 receptor, allowing repeated measurements of soluble ligands released by bacteria by appropriate excitation and detection;
   (c) a fluorescent heparin-like receptor, receptor for other natural cell surface molecule, or a custom synthesized receptor, with either type binding specific ligands to provide a Class-3 receptor, allowing repeated measurements of bacterial accumulation or accumulation of unique bacterial products based on fluorescent resonance transfer during appropriate excitation and detection; and
   (d) a mixed matrix such as a heparin-like receptor to bind bacteria combined with an α-hemolysin receptor conjugated to a fluorochrome to provide a Class-4 receptor, allowing repeated measurements of accumulation of unique bacterial products based on fluorescent resonance transfer during appropriate excitation and detection.

4. In respect to detection of the signal emanating from the biosensor, the prior art does not teach the use of fiberoptic probes to interrogate biosensors that are of special design and entirely separate from the probe, without placing the fiberoptic probe into the contents of each primary container.

5. In respect to collection of bacteria on, or in close proximity to, the biosensor, the prior art does not teach the use of synthetic materials or biomaterials to enhance probability of detecting such organisms.

The Examples illustrate how biosensors, as above, can be positioned in front of an optical window, accessible to a removable fiber-optic detector, while protected in a separate closed sub-container within the primary container. They are illustrative of the many uses of the invention, although the invention encompasses other biosensors, other membranes with open pores or gated-pores, other configurations, and other combinations of functional elements in the device. Examples of devices include reference to welding of a gated-pore membrane to a plastic construct. The invention is not limited by the plastic(s) used to form the device. The preferred welding process will depend on the plastic used to fabricate the construct, and the invention includes any method to assemble the device or incorporate it into the primary container, such as ultrasonic and radio-frequency welding, or other methods known to those skilled in the art. Examples illustrate the variety of materials that can be used to form gated-pore membranes or serve as biosensors, in one or more types of devices, and the invention is not limited in respect to specific compositions or analytes.

While examples provided illustrate detection of "unwanted agents", the principles disclosed also can be used to detect or measure accumulation of materials deemed to be beneficial to the system. An example would be signaling production of growth factors, a product of commercial value, by cells within a primary chamber.

The following list describes the FIGS. in greater detail:

FIG. 1 Schematic representation of a gated-pore membrane prepared using a microporous or capillary-track membrane and unique material to occlude the pores (e.g., as in U.S. Pat. No. 5,026,342).

Figure 2:
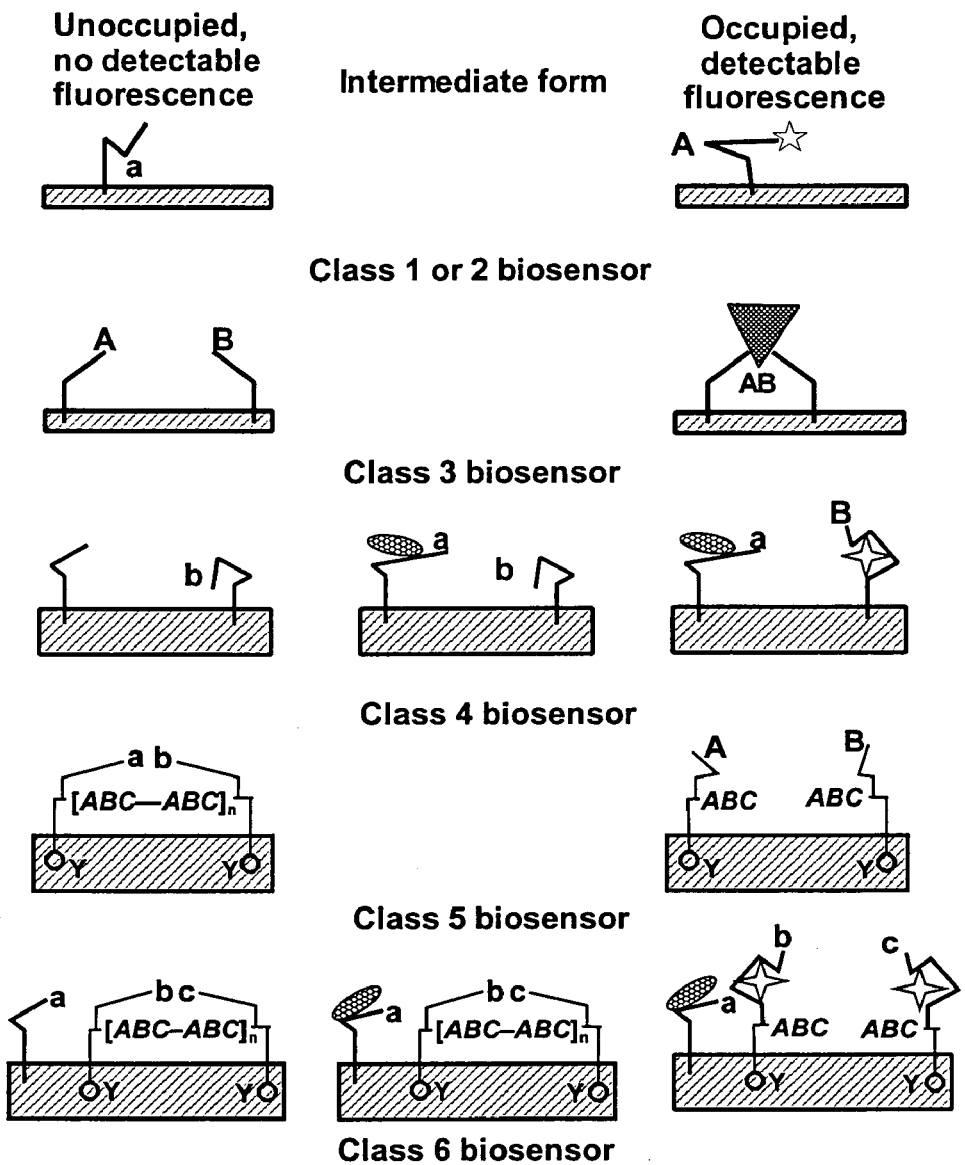
FIG. 2 is a schematic representation of the functioning of six classes of biosensors.

FIG. 2 Schematic representation of changes in a receptor-fluorescent reporter group upon change from unoccupied receptor to occupied receptor-ligand complex, listed by biosensor class as detailed in the specification. A reporter group that is non-fluorescent is designated with a lower-case letter and a reporter group that can fluoresce when excited with light of appropriate wavelength is designated with an upper-case letter.

Figure 3:
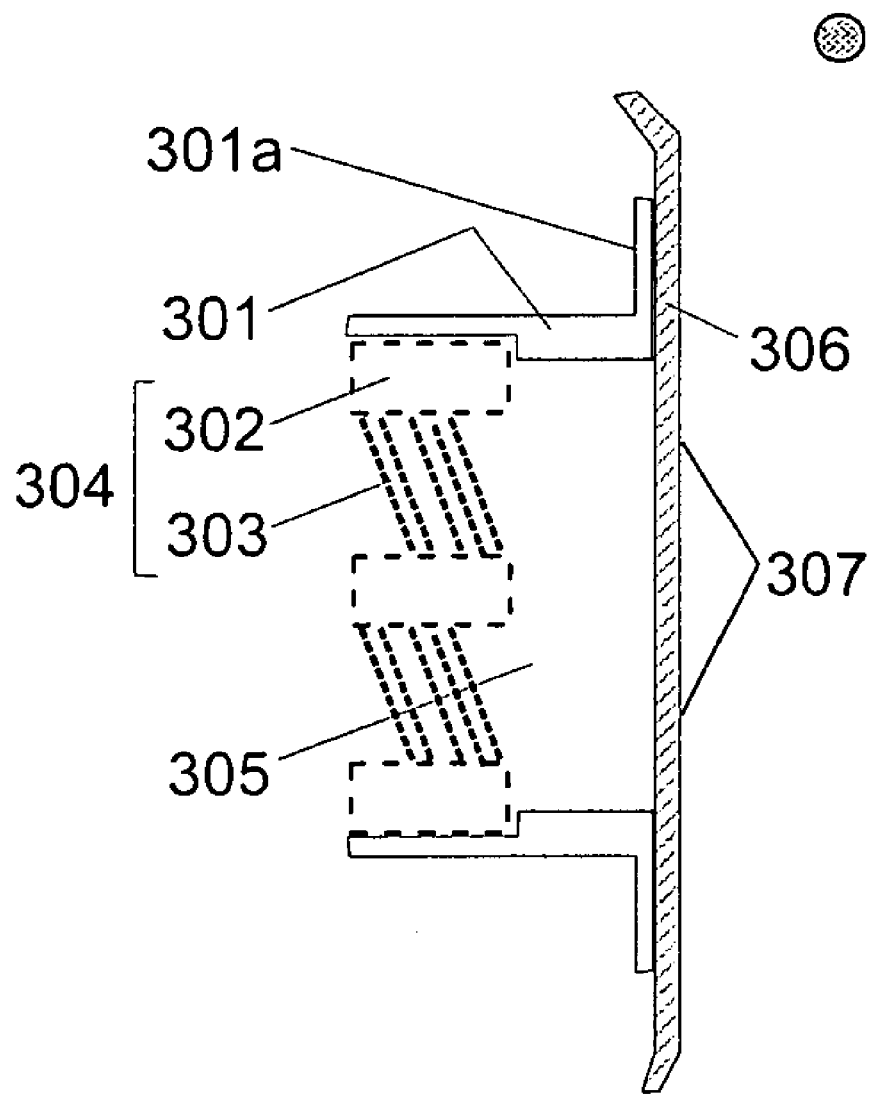
FIG. 3 is a schematic representation of a device according to the present invention for visual detection of a signal from a biosensor.

FIG. 3 Cross-section through a simple boat-shaped device as described in Example 1. The capillary-pore membrane (302) was processed with material (303) to plug the pores and make a gated-pore membrane (304). This membrane is bonded to a plastic construct (301) to form a cavity which then was filled with a biosensor (305) before the device was bonded via a flange (301a) to the primary container (306).

Figure 4:
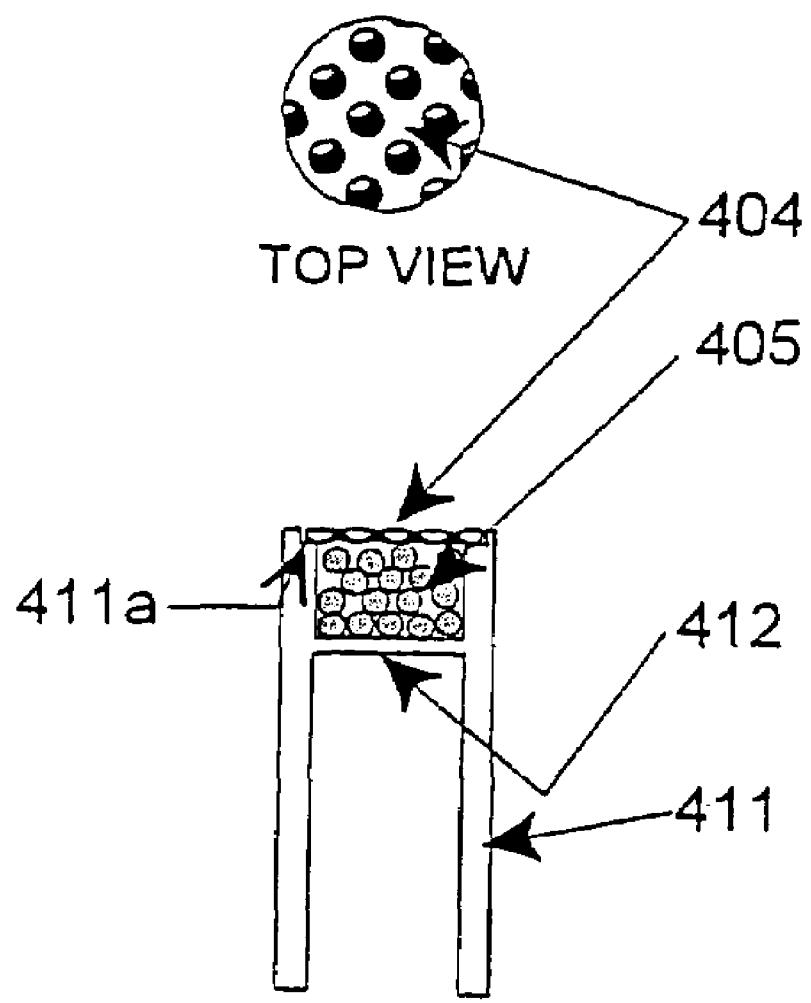
FIG. 4 is a schematic representation of a device according to the present invention for monitoring a change within a closed primary container, when visual detection of changes in the biosensor or configuration of the device is inappropriate.

FIG. 4 Longitudinal section through a device, and also a top view, as described in Example 2. The biosensor-compartment in a cylindrical construct (411) was filled with a biosensor (405). A gated-pore membrane (404) was bonded to a recessed surface (411a) to seal the biosensor in the device. The device then can be incorporated into the seam (420) of a primary container (not shown) so that the optical window (412) can be interrogated with a fiber-optic probe FIG. 5 Longitudinal section through a device, and also a top view, as described in Example 3. An optically clear cylindrical construct (511) was surrounded by an opaque outer concentric construct (515). The biosensor compartment was filled with a biosensor (505). A gated-pore membrane (504) was bonded to a recessed surface (515a) of the opaque outer concentric construct (515) to seal the biosensor in the device. The device then can be incorporated into the seam (520) of a primary container (not shown).

Figure 5:
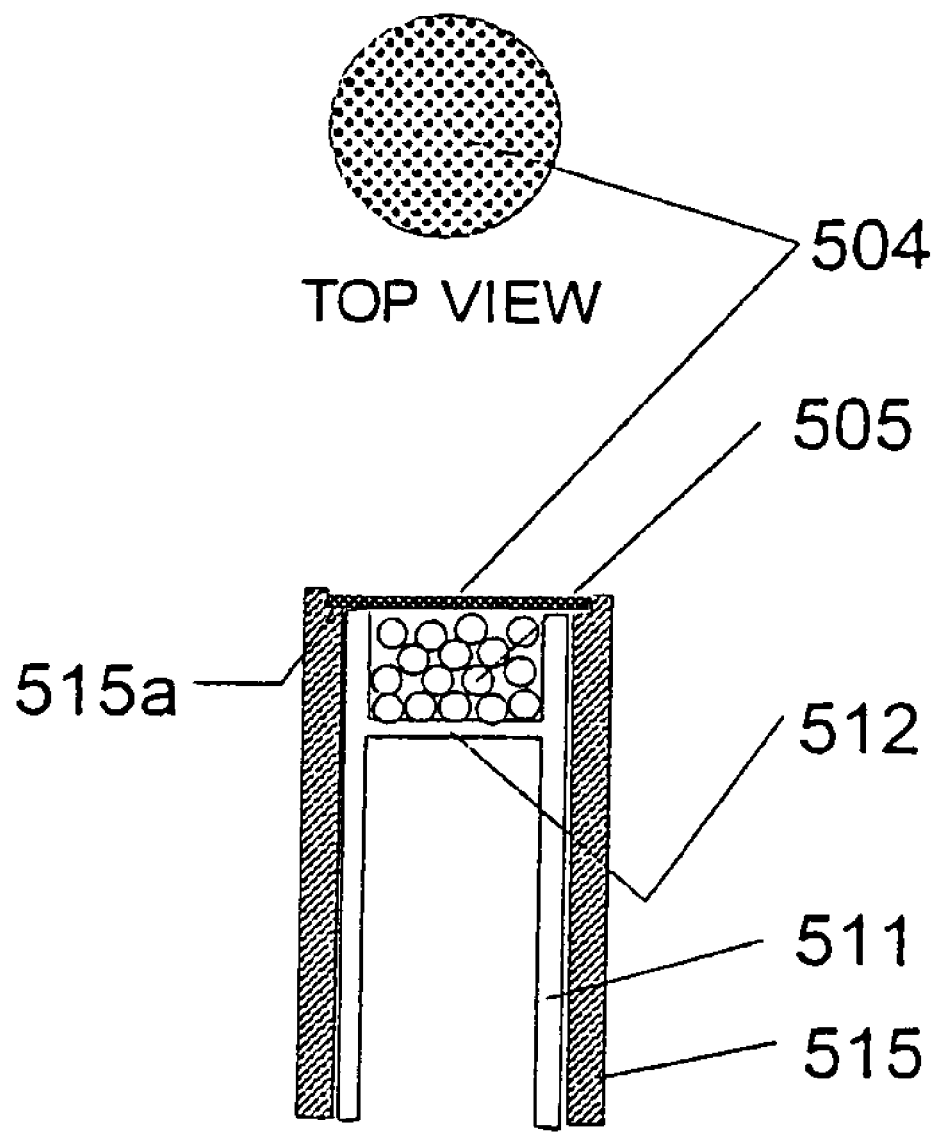
FIG. 5 is a schematic representation of a device according to the present invention with an outer opaque element.
Figure 6:
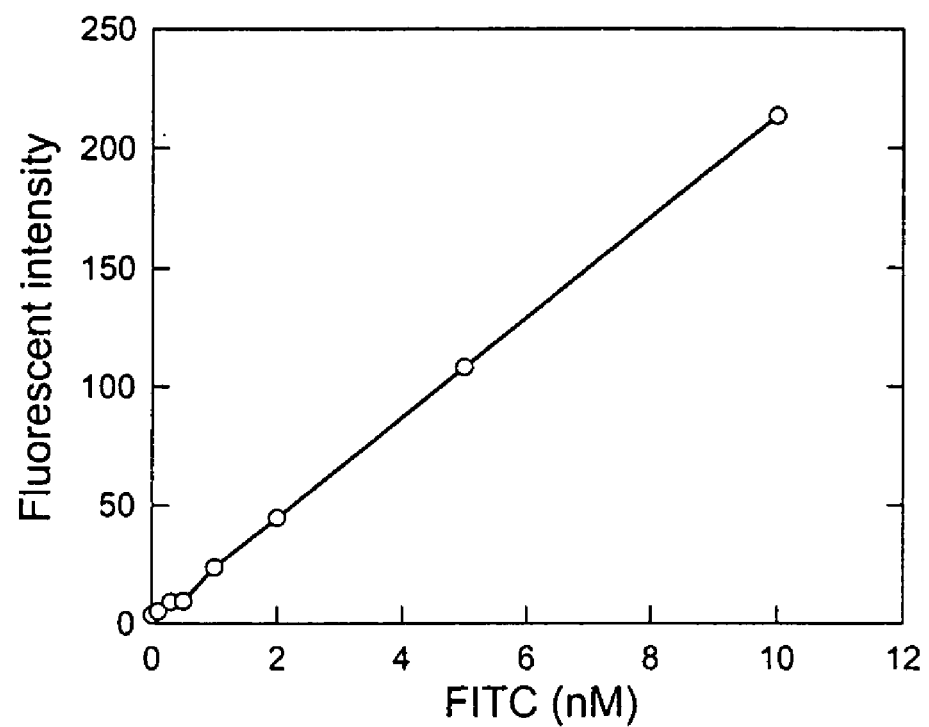
FIG. 6 is a graph of measured light intensity vs. concentration as measured in the device of FIG. 5.

FIG. 6 Intensity of fluorescence from a solution of fluorescein isothiocyanate (FITC) in a device as a function of concentration of FITC. Device as in FIG. 5; measurements with fiber-optic detector using excitation at 480 nm and detection at 535 nm (thousands of fluorescent units).

Figure 7:
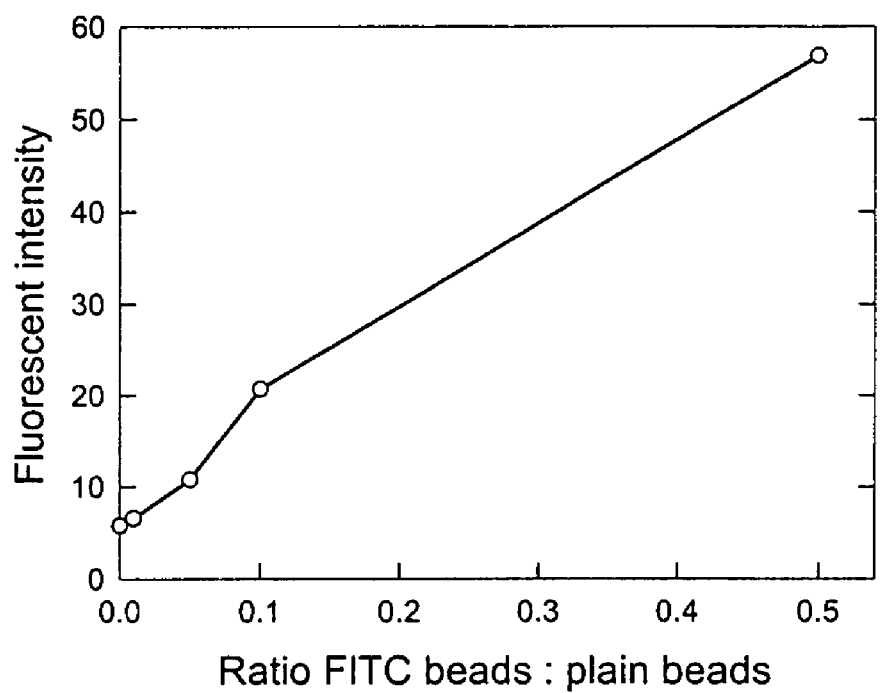
FIG. 7 is a graph of measured light intensity vs. ratio of labeled beads to plain beads as measured in the device of FIG. 5.

FIG. 7 Intensity of fluorescence from beads in a device as a function of the ratio of beads labeled with fluorescein isothiocyanate (FITC) to plain beads. Device as in FIG. 5; measurements with fiber-optic detector using excitation at 480 nm and detection at 535 nm (thousands of fluorescent units).

Figure 8:
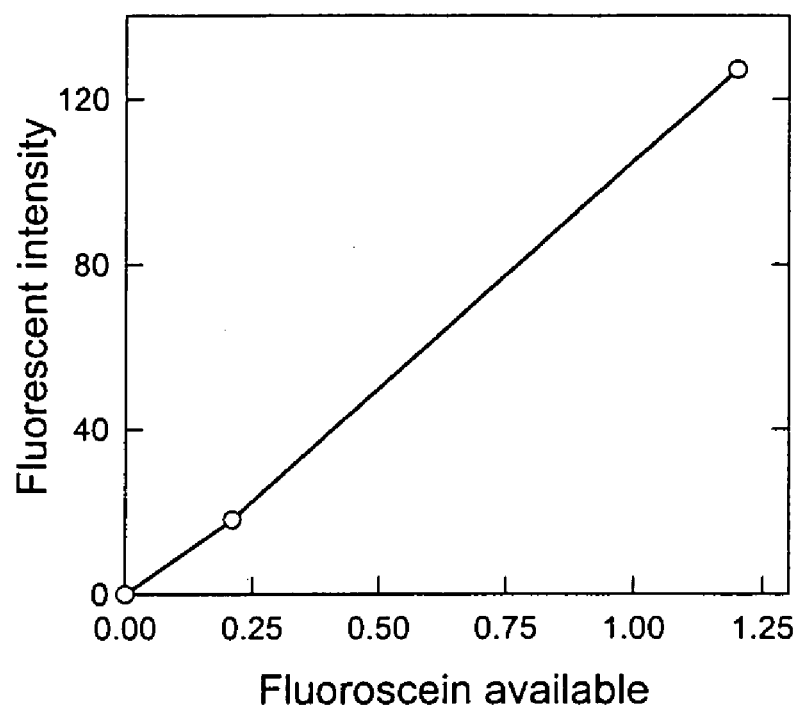
FIG. 8 is a graph of measured light intensity vs. available fluorescein as measured in the device of FIG. 5.
Figure 9:
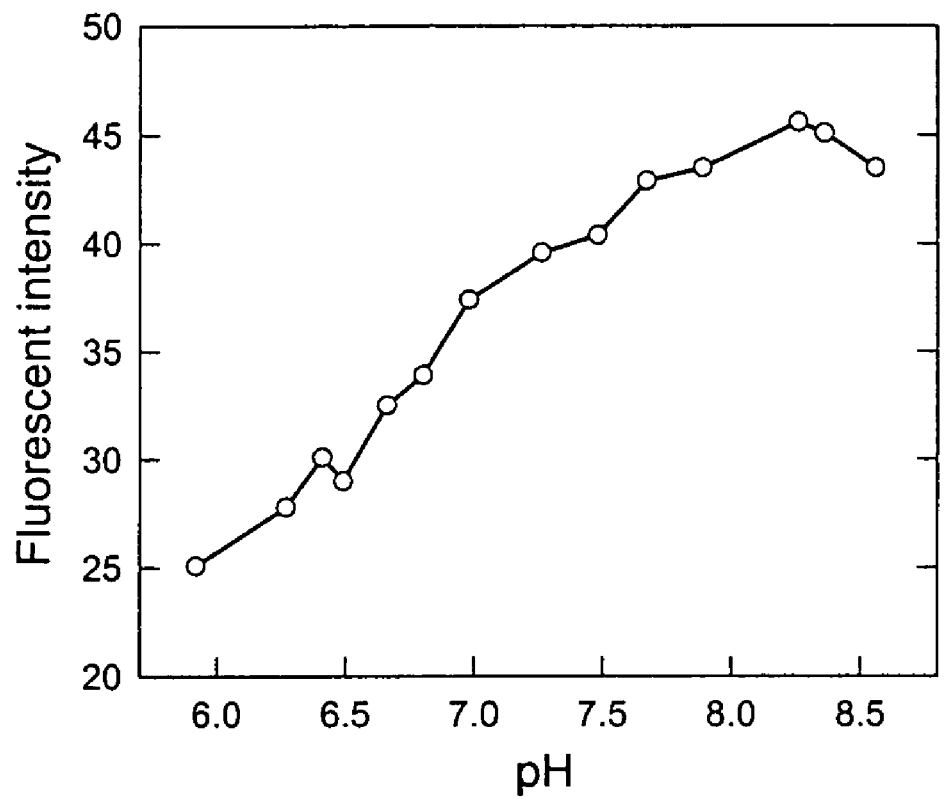
FIG. 9 is a graph of measured light intensity vs. pH as measured in the device of FIG. 5, showing pH responsiveness of FITC.

Fig. 8 Intensity of fluorescence from beads in a device as a function of their known content of fluorescein isothiocyanate (FITC). Known contents of FITC were equivalent to 0.00, 0.22 and 1.20 million molecules of FITC in solution. Device as in FIG. 5; measurements with fiber-optic detector using excitation at 480 nm and detection at 535 nm (millions of fluorescent units). FIG. 9 Intensity of fluorescence from beads, previously labeled with fluorescein isothiocyanate (FITC), in a device as a function of pH of the salts solution around the device and around the beads therein. Device as in FIG. 5; measurements with fiber-optic detector using excitation at 480 nm and detection at 535 nm (thousands of fluorescent units).

Figure 10:
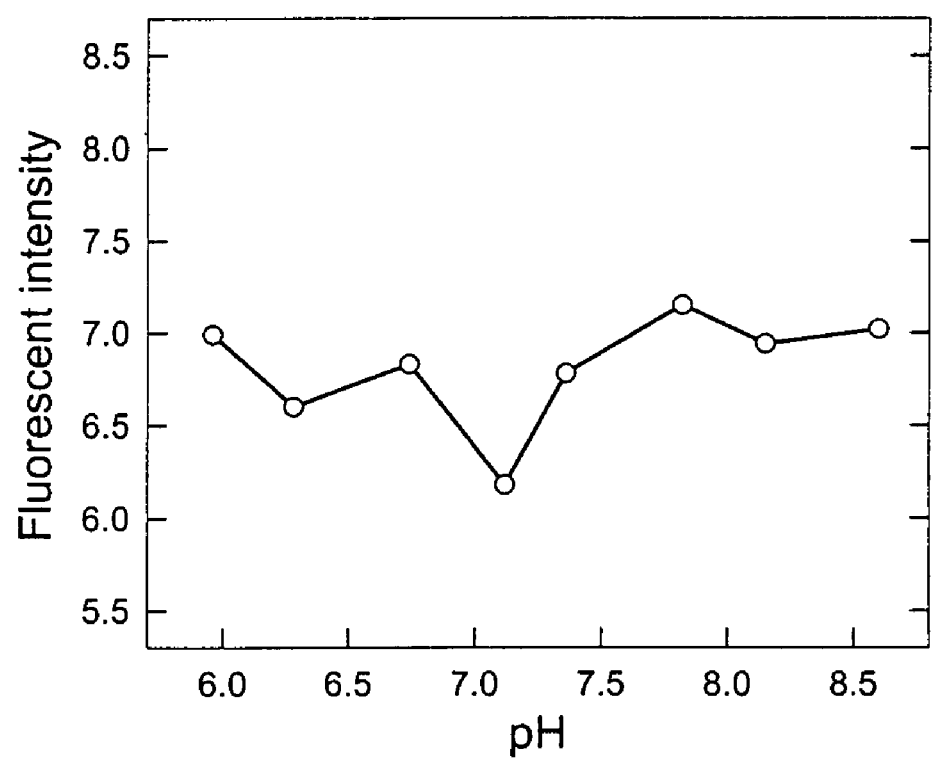
FIG. 10 is a graph of measured light intensity vs. pH as measured in the device of FIG. 5, showing pH non-responsiveness of phycoerythrin-cyanin-5 strepavidin.

FIG. 10 Minimal effect of pH of a salts solution on fluorescence from phycoerythrin-cyanin-5 strepavidin attached to beads. Device as in FIG. 5; measurements with fiber-optic detector using excitation at 480 nm and detection at $\geq$640 nm (thousands of fluorescent units).

Figure 11:
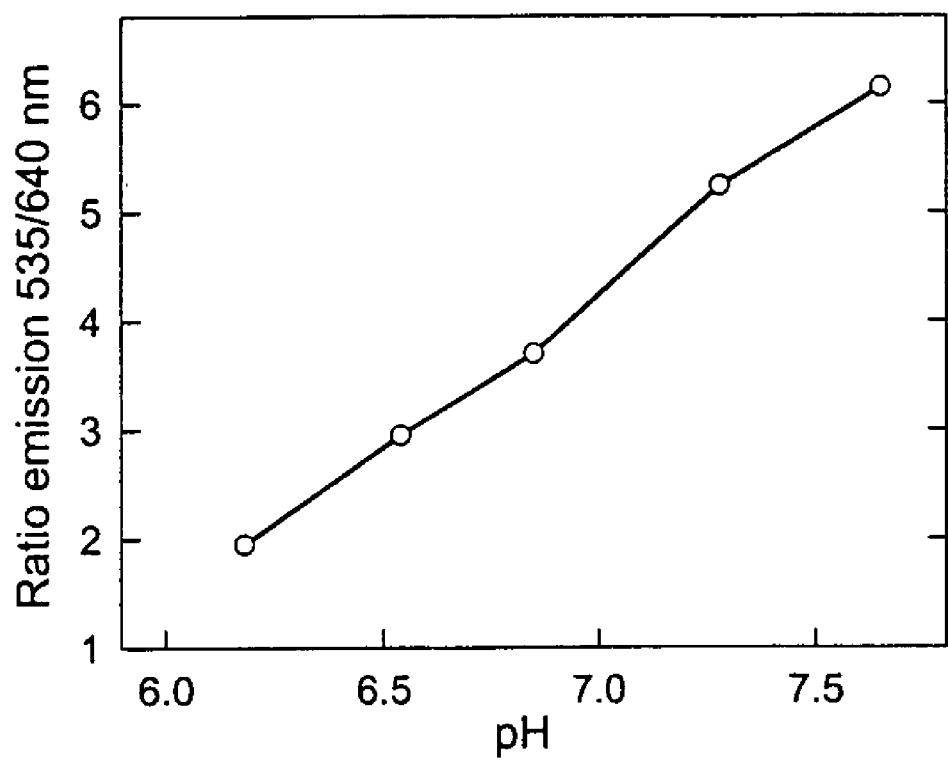
FIG. 11 is a graph of the ratio of two wavelengths of emitted light vs. pH as measured in the device of FIG. 5.
Figure 4A:
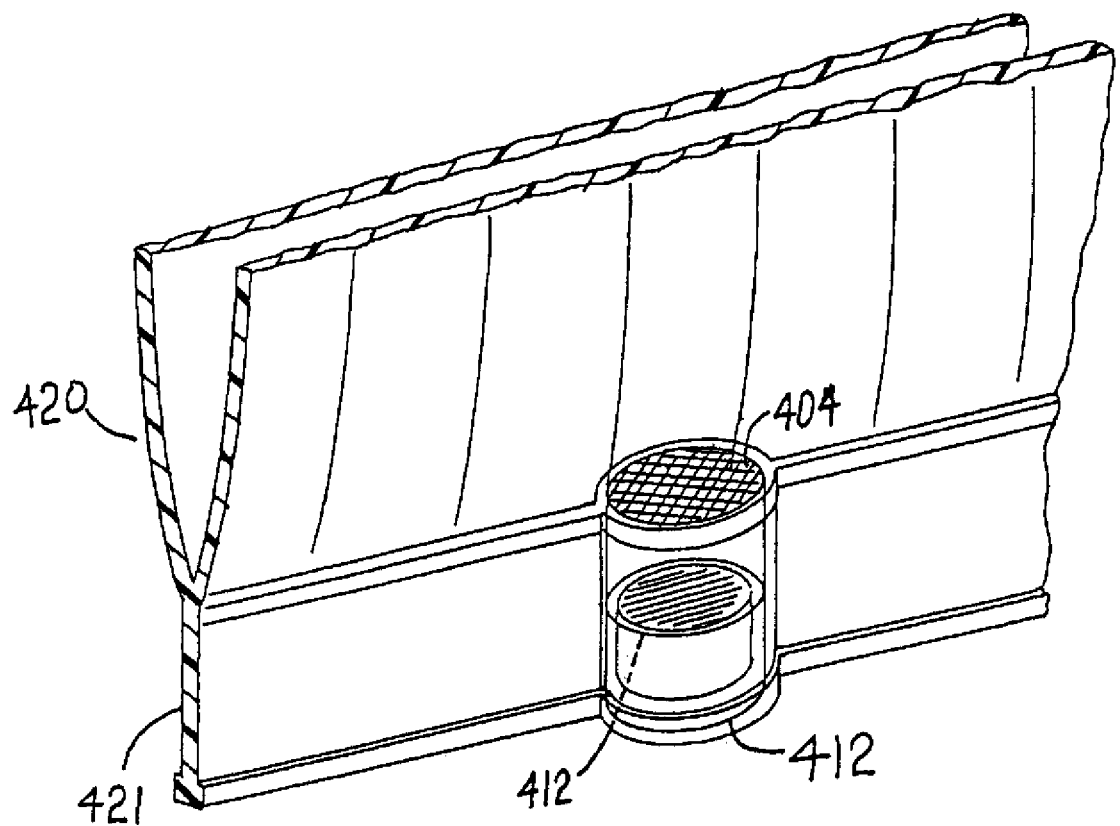
Figure 5A:
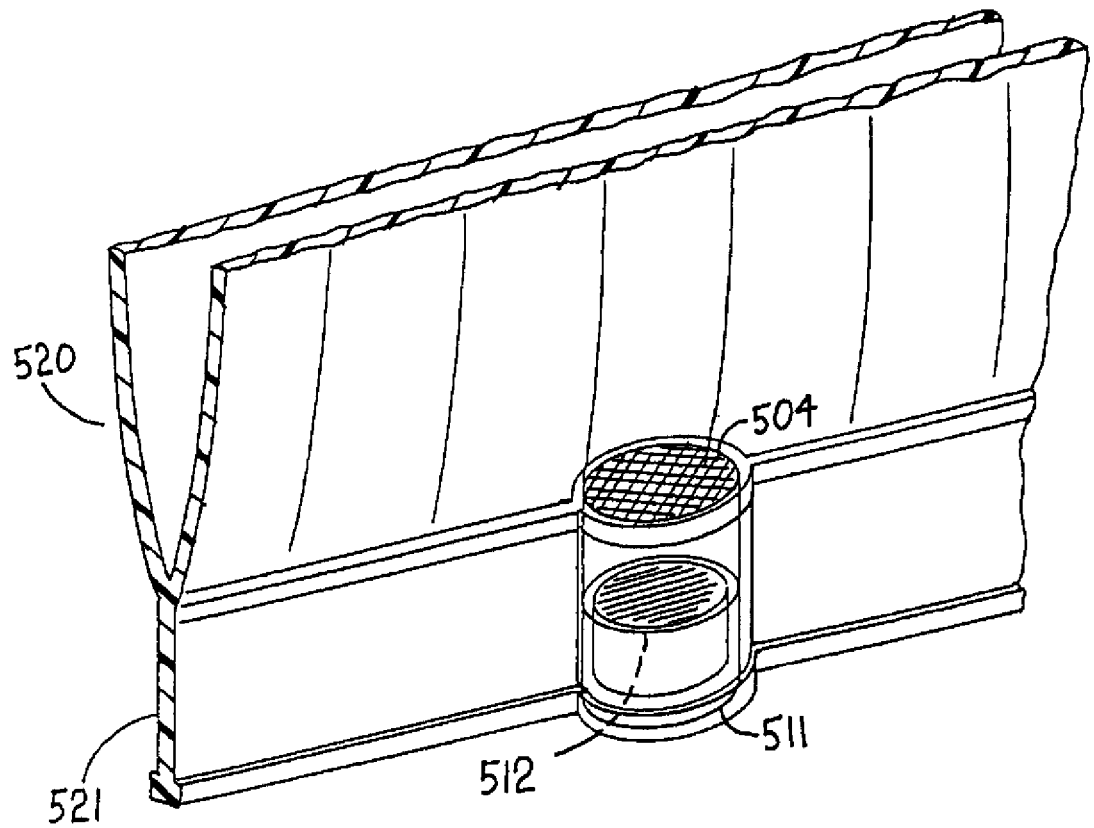

FIG. 11 Ratio of emissions from beads responsive to pH and non-responsive to pH can be used to normalize data for irregularities of response or color of the medium. The device contained a mixture of beads labeled with fluorescein isothiocyanate (pH responsive; FIG. 9) and phycoerytbrin-cyanin-5 strepavidin (pH non-responsive; FIG. 10). The ratio of emission at 535 nm and $\geq$640 nm was calculated as a function of pH of the salts solution around the device and around the beads therein. Device as in FIG. 5; measurements with fiber-optic detector using excitation at 480 nm and detection at 535 nm and $\geq$640 nm (raw values ranged between 75,000 and 135,000 relative fluorescent units).

EXAMPLE 1

A simple device (FIG. 3) can be used to monitor one of a variety of changes within a closed primary container. It is formed from a shallow, plastic construct (301) with an external flange (301a) on one side and a gated-pore membrane (304) welded to the other side. After filling the construct with a biosensor (305) providing a signal detectable by a human eye (e.g., plastic beads that change color when bathed in an aqueous fluid), the construct is welded to a convenient location on the wall of the primary container (306). This device depends on selectivity in response of the gated-pore membrane as the primary mechanism regulating change in a simple biosensor. When thus positioned, changes in the signal from the biosensor can be detected visually through a portion (307) of the primary container, without opening the primary container.

EXAMPLE 2

Another device (FIG. 4) can be used to monitor one of a variety of changes within a closed primary container, when visual detection of changes in the biosensor or the configuration of the device in Example 1 is inappropriate. This device can be of any convenient shape and formed from any plastic, but a cylindrical plastic construct formed from clear acrylic plastic is favored for some applications, and a clear optical window transmitting the portion of the spectrum of interest is essential. The device of FIG. 4 is a cylindrical acrylic construct (411) with a biosensor compartment formed by an optical window (412), a gated-pore membrane (404) responding to any aqueous environment, and the walls of the construct. After the biosensor compartment is filled with a biosensor (405) capable of detecting the desired change within the primary container, the gated-pore membrane is welded to the surface (411a) of a recess in the end of the construct. After the device is incorporated into a primary container, (not shown) and the container is filled with a suspension of cells of interest, the biosensor can be interrogated without opening the primary container, when desired, by positioning the tip of a separate fiber-optic probe (not shown), as known to those skilled in the art, against the optical window (412). This device uses the gated-pore membrane simply to protect and isolate the biosensor until the primary container is filled, for example with a cell suspension, after which the gates open in <30 minutes and selectivity in response to a predetermined analyte and intensity of signal are properties of the biosensor and amount of material impinging thereon.

EXAMPLE 3

A third device (FIG. 5) incorporates an opaque outer plastic element (515), with accommodation (515a) to weld a gated-pore membrane (504) to this part of the device, positioned around and bonded to an inner element (511) which is a clear plastic construct similar to the device of Example 2 and contains a biosensor (505) capable of detecting the desired change within the primary container. This device can be of any convenient shape and formed from any plastic, but a cylindrical concentric construct is favored for some applications. The outer opaque element (515) might be of colored polyvinyl chloride to shield the biosensor from stray light and facilitate welding the device into a polyvinyl chloride blood bag, and the inner element of clear plastic so that the optical window (512) will transmit the portion of the spectrum of interest. This device can be used to monitor one of a variety of changes within a closed primary container, when stray light might affect detection of the signal from the biosensor, by positioning the tip of a separate fiber-optic probe (not shown), as known to those skilled in the art, against the optical window (512). This device uses a gated-pore membrane to protect and isolate the biosensor until the primary container is filled and for a predetermined interval (e.g., 0.5, 2 or 5 days) thereafter or until a predetermined threshold of a specific change in contents of the primary container is reached (e.g., concentration of first analyte), after which the gates open and the biosensor begins to monitor changes in concentration of the same molecule or ion. triggering the gated-pore membrane. Alternatively, the biosensor can be used to monitor concentration of a second analyte with intensity of the signal from the biosensor dependent on properties of the biosensor and amount of second analyte impinging thereon.

EXAMPLE 4

Capability of a device as in FIG. 5 to detect changes in fluorescence was established. A commercial fiberoptic spectrometer (S2000-FL; Ocean Optic, Inc ) was equipped with optic filters suitable for desired analysis (excitation at 480 nm and detection of emission at 535 nm), and interfaced to a computer as recommended by the manufacturer. This was used to evaluate a series of solutions and particle suspensions. First, standard solutions of fluorescein isothiocyanate (FITC) were prepared and 0.075 ml aliquants were placed within the biosensor compartment (505). The intensity of fluorescence from FITC was recorded. There was a linear increase in measured intensity with increasing concentration of FITC (FIG. 6). Next, mixtures microspheres (6-8 micrometers, Spherotech Inc.) without and after conjugation with FITC were prepared. In succession, several ratios of labeled to unlabeled beads were placed into the biosensor compartment (505), in 0.05 ml. Intensity of fluorescence from FITC was recorded for each mixture. There was a linear increase of intensity of measured fluorescence from FITC as the proportion of labeled beads increased (FIG. 7). This established the capability of the external fiberoptic detector to correctly assess emission output from a chromophore, on a solid support as anticipated for biosensors accomplishing designated tasks in detection of known ligands, placed within the biosensor compartment.

EXAMPLE 5

A series of beads of known FITC content (Quantum 25-#825; Flow Cytometry Standards Corp) was purchased, and 0.05 ml of each suspension were placed in a device as in FIG. 5. A linear response was noted (FIG. 8). Importantly, the coefficient of variation for replicate measurements using the fiberoptic detector and beads (505) within the biosensor compartment was within the coefficient of variation provided for these standards by the supplier, and presumably measured under optimum conditions. To provide a relation to data of FIG. 6, the bead suspensions also were evaluated relative to a standard curve of known amounts of FITC in a microplate fluorometric reader. The highest concentration of beads tested was equivalent to 4 nM FITC.

EXAMPLE 6

Beads suitable for use as an "optical bench" were prepared by covalent attachment of dextran (#1820; Molecular Probes) containing both FITC and lysine to 10 micrometer diameter carboxylate beads (Polysciences, Inc), using standard carbodiimide coupling chemistry. This provided an immobilized fluorophore, known by those versed in the art to be responsive to pH through the FITC function and suitable for analysis of pH. Localization of the FITC at a sufficient distance from the bead surface, by means of the dextran, eliminated problems related to the well-known surface effects on fluorescence. The biosensor cavity was filled with the bead suspension (505), and the membrane (504) attached. Beads were allowed to settle onto the optical window (512). The filled cylindrical construct then was placed into a phosphate buffered saline solution with pH and temperature (21.5±0.5 C.) monitored using a standard laboratory meter. Acid or base was added to change the pH, and fluorescence intensity was measured after allowing 30-60 minutes for equilibration. Resulting data (FIG. 9) clearly established that pH in the microenvironment of a biosensor, within the device of FIG. 5, can be measured with an external detector. Most importantly, the anticipated pH-related change in intensity of fluorescence detected was similar to published data (i.e., linear 2.0-2.5 fold increase in intensity between pH 6.0 and pH 8.0). Additional experiments (data not presented) established, as in Example 4, that unlabeled beads could be added to fill the chamber without degradation of signal intensity. Note that we allowed a 30 minute response time to insure stability of conditions around the beads after adding acid or base. However, response time could be reduced substantially by agitation of the primary container, or by design of the integral sensor to increase the amount of gated-pore membrane enclosing the biosensor cavity and thus reduce time for protons or other ligands to enter and interact with the biosensor.

EXAMPLE 7

Samples to be analyzed might contain components that will interfere with direct fluorescence measurements. For example, it is well-known that human plasma can contain variable amounts of "yellow" materials that could absorb incident light at the excitation wavelength. Optical density at 480 nm was measured for 13 different samples of human blood plasma (cell free), and absorbance averaged 0.554 (standard deviation was 0.428; range from 0.12 to 1.30), but was much lower at >500 nm. Clearly, this wide a range in absorbance could affect the light available for excitation of a biosensor incorporating, for example, FITC as the signal moiety.

Use of an internal standard is a classic analytical approach to reduce impact of non-uniformity in the matrix of a signal system. A second detector bead system (B-2) could be constructed so that it shared excitation wavelength with the primary bead (B-1; e.g., FITC), but emitted at a distinctly different wavelength than B-1 and was unaffected by the ligand altering response of the biosensor of bead B-1 (e.g., protons in case of FITC). This would allow excitation of both fluorochromes concurrently under identical conditions, and alternating measurement of emission from B-1 and B-2. Calculation of the ratio B-1/B-2 would allow detection of changes in emission from B-1 without substantial impact from a wide range in absorbance of exciting light by components in the matrix. This approach should be useful with products ranging from blood cells to orange juice.

To illustrate utility of such an approach, a general bead coating was developed by covalently attaching biotin-dextran (D-1956; Molecular Probes) to 10 micrometer diameter carboxylate beads (Polysciences, Inc.), using standard carbodiimide coupling chemistry. This provided a common attachment site on the beads for avidin-strepavidin conjugates. Assuming beads of biosensor B-1 used FITC, materials suitable for service as B-2 should be excited (absorb) at 480 nm, emit at a wavelength distinct from 535 nm, and have a response independent of pH. Examples include reagents available from Coulter Diagnostics such as: Strepavidin-PC5 (strepavidin conjugated to phycoerythrin-cyanin 5; excitation 486-580; emission 660-680) and EDC (strepavidin conjugated to phycoerythrin-Texas Red7-x; excitation 486-580; emission 610-630). It is well-known to those versed in the art that many other combinations can be used to correct for effects on either excitation or emission wavelengths. We used the PC-5 system and evaluated freedom from a pH-driven shift in emission. As evident in FIG. 10, with excitation at 480 nm and emission (from the cyanin-5) measured using a ≧640 long-pass filter, there was little change in intensity of emission between pH 6.0 and pH 8.5. This was very different from the response of FITC (FIG. 9).

EXAMPLE 8

The concept of a ratio correction (see above) and observations from Examples 6 and 7 were directly tested to illustrate utility of a ratiometric analysis of pH using an integral sensor as in FIG. 5. Two different biosensor beads were prepared, mixed in an appropriate ratio, and placed (505) within the cavity of the integral sensor, fabricated from a type of acrylic plastic known to have optical properties appropriate for this application. The gated-pore membrane (504) was fabricated from capillary-pore membrane stock (RoTrac® polyester membrane, Oxyphen AG; 3 μm pore diameter; 60 g/m² polyester backing) using methylcellulose to occlude the pores, and the resulting gated-pore membrane was used to seal beads B-1 and B-2 into the device. The pH sensitive biosensor (B-1) was FITC dextran attached to a polystyrene support (as in Example 6) and the pH insensitive biosensor (B-2) was EDC-strepavidin attached to biotin/dextran polystyrene (see Example 7). The same fiberoptic fluorometer (S2000-FL; Ocean Optic, Inc.) was used to interrogate the device, as pH of the salts solution was changed as in Example 6. The system was excited at 480 nm and emission read with both the 535 nm and ≧640 nm filters. Resultant data (FIG. 11) show excellent linearity of response in the range of interest to blood banks, pH 6.0 to 7.0. Use of human erythrocytes for infusion into a recipient is ill advised if the contents are at pH ≦6.2. Detection of pH within a primary container (i.e., conventional plastic blood bag) containing erythrocytes or platelets should be easy if the bag was fabricated to include a device as in Example 8. Resultant measurements of pH should not be affected by bag-to-bag differences in background colors typical of blood products.

EXAMPLE 9

A device, fabricated as in FIG. 4 or 5, can use a Class-5 biosensor (see FIG. 2) to detect accumulation of a protease secreted by bacteria within a closed primary container. Active elements of the integral detector would be as detailed above, except that plastic beads would be coated with "doped" lipid to provide a Class-5 biosensor. The lipid would be "doped" with an enzyme substrate synthesized with fluorescent moieties ("a" and "b"; inhibiting each other's emission because of proximity) incorporated on either side of the proteolytic cleavage site. Thus, fluorescence of the enzyme substrate is mutually inhibited by close proximity of receptors "a" and "b" if the substrate molecule is intact. However, enzymatic cleavage of the substrate allows separation of the fluorescent moieties associated "a" and "b" and emission of a detectable signal during interrogation with exciting light of the appropriate wavelength. One example of such a biosensor suitable for attachment to an avidin-strepavidin coated bead is: biotin-(6-aminohexanoicacid)-(6-aminohexanoicacid)-(6-aminohexanoicacid)-Lys(Tamara)-(6-aminohexanoicacid)-Ala-Phe-Glu-Ala-Leu-(6-aminohexanoicacid)BCys(Texas Red)-Gly-COOH. The "-Ala-Phe-Glu-Ala-Leu-" sequence should be useful for detecting proteases known to be secreted from a variety of bacteria including *Bacillus cereus, Escherichia coli, Poteus mirabilis, Serratia marcescens, Staphyloccous aureus,* and *Streptococcus* species. Other similar substrates, exhibiting appropriate susceptibility to hydrolases, can be designed as appropriate, using assumptions known to those skilled in the art.

EXAMPLE 10

A device, fabricated as in FIGS. 4 or 5, can use a Class-6 biosensor (see FIG. 2) to accumulate bacteria and increase sensitivity for detection of a protease secreted by bacteria within a closed primary container. Active elements of the integral detector would be as detailed above, except that plastic beads "doped" lipid would be used to fabricate a Class-6 biosensor. A material binding the bacteria of interest (e.g., fibronectin, laminin, type-4 collagen) would serve as receptor "a" (see FIG. 2). The coating of this biosensor also would include an enzyme substrate synthesized with fluorescent moieties ("b" and "c"; inhibiting each other's emission because of proximity) incorporated on either side of the proteolytic cleavage site. As described in Example 9, the enzyme substrate might be: biotin-(6-aminohexanoicacid)-(6-aminohexanoicacid)-(6-aminohexanoicacid)-Lys(Tamara)-(6-aminohexanoicacid)-Ala-Phe-Glu-Ala-Leu-(6-aminohexanoicacid)BCys(Texas Red)-Gly-COOH. *Streptococus pyrogenes* are known to bind to the fibronectin serving as receptor "a" and secrete proteases that can cleave the -Ala-Phe-Glu-Ala-Leu- peptide integral to receptor "b" and "c", removing the proximity inhibition to their fluorescence. Consequently, as *Streptococus pyrogenes*, or other bacteria, proliferated in the primary container they would accumulate on the biosensor and the fluorescent signal detectable on probing with a fiberoptic fluorometer would reflect the extent of bacterial contamination in the primary container.

This invention is very broad and the examples presented herein are illustrative, but do not limit the scope of the invention.

REFERENCES

U.S. Patents

U.S. Pat. No. 5,261,870 1991 Hammerstedt et al. Separation barrier with plugged pores.

U.S. Pat. No. 5,368,712 1994 Tomich et al. Biological mimetic synthetic ion channel transducers.

U.S. Pat. No. 5,605,809 1997 Komorlya and Packard Compositions for the detection of proteases in biological samples and methods of use thereof.

U.S. Pat. No. 5,7111,915 1998 Siegmund et al. Optical solid-phase biosensor based on polyionic layers labeled with fluorescent dyes.

OTHER PUBLICATIONS

Abraham S N, Beachey E H, Simpson W A. 1983 Adherence of *Streptococcus pyrogenes, Escherichia coli*, and *Pseudomonas aeruginosa* to fibronectin-coated and uncoated epithelial cells. Infect Immun 41:1261-1268.

Agayn V I, Walt D R. 1993 Fibre-optic sensor for continuous monitoring of fermentation pH. Biotechnology 11:726-729.

Anonymous. 1999a Technote #204 Adsorption to microspheres. Banks Laboratories, Fishers Ind.

Anonymous. 1999b Technote #205 Covalent Coupling. Banks Laboratories, Fishers Ind.

Anonymous. 1999c Technote #302 Molecular Biology. Banks Laboratories, Fishers Ind.

Anonymous. 1999d Technote #301 Immunological Applications. Banks Laboratories, Fishers Ind.

Bark SJ, Hahn K M. 2000 Fluorescent indicators of peptide cleavage in the trafficking compartments of living cells: Peptide site specifically labeled with two dyes. Methods 20:429-435.

Barrett SP. 1988 Bacterial adhesion to intravenous cannulae: influence of implantation in the rabbit and of enzyme treatments. Epidem Inf 100:91-100.

Barth E, Myrvik QM, Wagner W, Gristina AG. 1989 In vitro and in vivo comparative colonization of *Staphyloccus aureus* and *Staphyloccus epidermis* on orthopaedic implant materials. Biomaterials 10: 325-328.

Blajchmann MA. 1998 Bacterial contamination and proliferation during the storage of cellular blood products. Vox Sang 74:155-159.

Cavinato AG, Mayes DM, Ge Z, Callis JB. 1990 Noninvasive method for monitoring ethanol in fermentation processes using fibre-optic near-infrared spectroscopy. Anal Chem 62:1977-1982.

Giuliano KA, Taylor DL. 1998 Fluorescent-protein biosensors: new tools for drug discovery. Tibtech 16:135-140.

Godwin HA, Berg JM. 1996 A fluorescent zinc probe based on metal-induced peptide folding. J Amer Chem Soc 118: 6514-6515.

Herrmann M, Vandaux PE, Pittet D, Auckenthaler R, Lew PD, Schumacher-Perdreau F, Peters G, Waldvogel FA. 1988 Fibronectin, fibrinogen, and laminin act as mediators of adherence of clinical *Staphylococcal* isolates to foreign material. J Infect Disease 158:693-701.

Hogt AH, Dankert J, DeVris JA, Feijen J. 1983 Adhesion of coagulase-negative *Staphylocci* to biomatierals. J Gen Microbiol 129:2959-2968.

Hogt AH, Dankert J, Feigen J. 1986 Adhesion of coagulase-negative *staphylococci* to methacrylate polymers and copolymers. J Biomed Mater Res 20:533-545.

Holtzer A. 1994 Application of old and new values of -helix propensities to the helix-coil transition of poly(L-glutamic acid). J Amer. Chem. Soc 116:10837-10838.

Hughes-Despointes BMP, Scholtz J M, Baldwin RL. 1993 Helical peptides with three pairs of Asp-Arg and Glu-Arg residues in different orientations and spacings. Polymer Sci 2:80-85.

Ito Y, Kotera S, Inaba M, Kono K, Imanishi Y. 1990 Control of pore size of polycarbonate membrane with straight pores by poly(acrylic acid) grafts. Polymer 31:2157-2161.

Ito Y, Inaba M, Chung D-J, Imanishi Y. 1992. Control of water permeation by pH and ionic strength through a porous membrane having poly(carboxylic acid) surface grafted. Macromolecules 25: 7313-7316.

Ito Y, Ochiai Y, Park Y S, Imanishi Y. 1997 pH-sensitive gating by conformational change of a polypeptide brush grafted onto a porous polymer membrane. J Amer Chem Soc 119: 1619-1623.

Kar S, Arnold MA. 1995 Fibre-optic chlorine probe based on fluorescence decay of N-(6-methoxyquinolyl)-acetoethyl ester. Talanta 42:663-670

Kinoshita T, Kakiuchi T, Takizawa A, Tsujita Y, Oya M., Iizuka Y, Iwatsuki M. 1994 Solute permeability enhancement at a specific pH by an amphiphlic copolypetide membrane. Macromolecules 27:1389-1394.

Kuusela P, Vartio T, Vuento T, Myhre E B 1985 Attachment of *Staphylococci* and *Streptococci* on fibronectin, fibronectin fragments, and fibrinogen bound to a solid substrate. Infect Immuni 50:77-81.

Laakel M, Bouchard M, Lagace J. 1996 Measurement of mouse anti-phospolipid antibodies to solid-phase microspheres by both flow cytofluorometry and Alcian blue-pretreated microtitre plates in ELISA. J Immun Meth 190: 267-273.

Lee, J-H. 1999 FDA's surveillance for bacterial safety of blood. Proc FDA Workshop on Bacterial Contamination of Platelets. Rockville, Md.

Mackenzie A M R, Rivera-Calderon R L. 1985 Agar overlay method to measure adherence of *Staphylococcus epidermis* to four plastic surfaces. Appl Environ Microbiol 50:1322-1324.

Maeda M, Kimura M, Hareyama Y, Inoue S. 1984 pH-dependent ion transport across polymer membrane. pH-induced reversible conformational change of transmembrane poly (L-aspartic acid) domain in polymer membrane. J Amer Chem Soc 106:250-251.

Marose S, Lindemann C, Scheper T. 1998 Two-dimensional fluorescence spectroscopy: A new tool for on-line bioprocessing monitoring. Biotechn Prog 14:63-74.

Marose S, Lindeman C, Ulber R, Scheper T. 1999 Optical sensor systems for bioprocess monitoring. Tibtech 17:30-34.

McHugh T M. 1994 Flow microsphere immunoassay for the quantitative and simultaneous detection of multiple soluble analytes. Meth Cell Biol 42:575-595.

Morgan C L, Newman D J, Price C P. 1996 Immunosensors: technology and opportunities in laboratory medicine. Clin Chem 42:193-209

Nolan J P, Lauer S, Prossnitz E R, Sklar L A. 1999 Flow cytometry: a versatile tool for all phases of drug discovery. DDT 4:173-180.

Sackmann, E. 1996 Supported membranes: scientific and practical applications. Science 271:43-48.

Song X, Swanson B I. 1999 Direct, ultrasensitive and selective optical detection of protein toxins using multivalent interactions. Anal Chem 71:2097-2107.

Song X, Nolan JP, Swanson BI. 1998 Optical biosensor based on fluorescence resonance energy transfer: Ultasensitive and specific detection of protein toxins. J Amer Chem Soc 120:11514-11515.

Spek E J, Gong Y, Kallenbach N R. 1995 Intermolecular interactions in helical oligo- and poly(L-glutamic acid) at acidic pH. J Amer Chem Soc 117:10773-10774.

Speziale P, Raucci G, Visai L, Switalski L M, Timpl R, Hook M. 1986 Binding of collagen to *Staphylococcus aureus* Cowan 1. J Bact 167:77-81.

Springer-Keller U E. 1997 Ion- and substrate-selective optode membranes and optical detection modes. Sensors Actuators B 38-39, 68-77.

St Pierre Y, Desrosiers M, Tremblay P, Esteve P-O, Opdenakker G. 1996 Flow cytometric analysis of gelatinase B (MMP-9) activity using immobilized fluorescent substrate on microspheres. Cyotmetry 25: 374-380.

Tartakovsky B, Sheintuch M, Hilmer J-M, Scheper T. 1996 Application of scanning fluorometry for monitoring of a fermentation process. Biotechnol Prog 12:126-131.

Tyagi S, Kramer F R. 1996 Molecular beacons: probes that fluoresce upon hybridization. Nature Biotech 14:303-308.

Urbano E, Offenbacher H. Wolfbeis O S. 1984 Optical sensor for continuous determination of halides. Anal Chem 56:427-429.

Urry D W. 1997 Physical chemistry of biological free energy transduction as demonstrated by elastic protein-based polymers. J Phys Chem 1001B:11007-11028.

Vaccari G, Dosi E, Campi A L, Gonzalez-Vara R, Matteuzzi D, Mantovani G. 1994 A near-infrared spectroscopy technique for the control of fermentation processes: An application to lactic acid fermentation. Biotech Bioengin 43:913-917.

Vercellotti G M, McCarthy J B, Lindholm P, Peterson P K, Jacob H S, Furcht L T. 1985 Extracellular matrix proteins (fibronectin, laminin and type IV collagen) bind and aggregate bacteria. Amer J Pathol 120:13-21.

Weigl B H, Holobar A, Trettnak W, Klimant I, Kraus H, O'Leary P, Wolfbeis O S. 1994 Optical triple sensor for measuring pH, oxygen and carbon dioxide. J Biotech 32:127-138.

Xu Z, Rollins A, Alcala R, Marchant R E. 1998 A novel fibre-optic pH sensor incorporating carboxy SNAFL-2 and fluorescent wavelength-ratiometric detection. J Biomed Materials Res 39: 9-15.

The invention claimed is:

1. A sensor device, comprising:
 a biosensor comprising a receptor bound on a solid substrate;
 a sensor compartment having an interior and an exterior, and enclosing the biosensor, the sensor compartment having a surface allowing external viewing of the biosensor; and
 a separation barrier forming at least a portion of the sensor compartment, the separation barrier being selected from the group consisting of a fibril membrane, a microporous membrane and a capillary-pore membrane, the separation barrier having at least one pore allowing fluid communication between the interior and the exterior of the sensor compartment, wherein the biosensor further comprises a detector molecule and signal material which are each attached to a surface of the biosensor wherein the detector molecule and signal material are selected from the group consisting of a) a combination of a first fluorescent receptor and a second fluorescent receptor, the second fluorescent receptor emitting detectable light of a unique wavelength on excitation by fluorescent resonance transfer by the first fluorescent receptor; b) a combination of a first receptor and a second receptor, the first receptor binding a cell and the second receptor undergoing a detectable spectral change in response to material released by the cell bound to the first receptor; c) a combination of two inhibited fluorescent groups linked by an enzymatic cleavage site, and wherein enzymatic action cleaves the enzymatic cleavage site and releases the fluorescent inhibition; and d) a combination of a first receptor and a second receptor, the first receptor binding a cell capable of releasing an enzyme and the second receptor being an inhibited fluorescent group wherein the enzyme releases the fluorescent inhibition.

2. The sensor device of claim 1, wherein the separation barrier separates the interior of the sensor compartment from a primary container.

3. The sensor device of claim 2, wherein the primary container is closed for analysis.

4. The sensor device of claim 1, wherein the at least one pore which allows fluid communication between the interior and exterior of the sensor compartment is occluded with a responsive material.

5. The sensor device of claim 4, wherein the responsive material is selected from the group consisting of cellulosics, non-cellulosic non-protein polymers, protein polymers, lipid bilayers, and lipid-containing composites.

6. The sensor device of claim 4, wherein the responsive material exhibits a response selected from the group consisting of eroding, dissolving, and changing three-dimensional form.

7. The sensor device of claim 6, wherein the response results from a change selected from the group consisting of a change in solvent concentration, a change in pH, a change in temperature, bacterial action, endotoxin action, enzymatic action, and contact with water.

8. The sensor device of claim 1, wherein the sensor compartment has walls comprised of an opaque material.

9. The sensor device of claim 1, wherein the bioactive detector molecule and signal material are a fluorescent receptor complex.

10. The sensor device of claim 1, wherein the bioactive detector molecule and signal material are a fluorochrome-receptor complex.

11. The sensor device of claim 1, wherein the device is capable of aseptic operation.

12. The sensor device of claim 1, wherein the external viewing is remote viewing.

13. A sensor device, comprising:
 a biosensor comprising a receptor bound on a solid substrate;

a sensor compartment having an interior and an exterior, and enclosing the biosensor, the sensor compartment having a surface allowing external viewing of the biosensor; and a separation barrier fonning at least a portion of the sensor compartment, the separation barrier being selected from the group consisting of a fibril membrane, a microporous membrane and a capillary-pore membrane, the separation barrier having at least one pore allowing fluid conunnunication between the interior and the exterior of the sensor compartment, wherein the biosensor further comprises a bioactive detector molecule and signal material which are each attached to a surface of the biosensor wherein the bioactive detector molecule and signal material are selected from the group consisting of a) a combination of a first fluorescent receptor and a second fluorescent receptor, the second fluorescent receptor emitting detectable light of a unique wavelength on excitation by fluorescent resonance transfer by the first fluorescent receptor; b) a combination of a first receptor and a second receptor, the first receptor binding a cell and the second receptor undergoing a detectable spectral change in response to material released by the cell bound to the first receptor; c) a combination of two inhibited fluorescent groups linked by an enzymatic cleavage site, and wherein enzymatic action cleaves the enzymatic cleavage site and releases the fluorescent inhibition; d) a combination of a first receptor and a second receptor, the first receptor binding a cell capable of releasing an enzyme and the second receptor being an inhibited fluorescent group wherein the enzyme releases the fluorescent inhibition; and e) a receptor that binds a material, such that upon binding the material, spectral features of the receptor are altered.

* * * * *

UNITED STATES PATENT AND TRADEMARK OFFICE
CERTIFICATE OF CORRECTION

PATENT NO. : 7,407,796 B2
APPLICATION NO. : 10/840178
DATED : August 5, 2008
INVENTOR(S) : Hammerstedt et al.

Figure 4A:
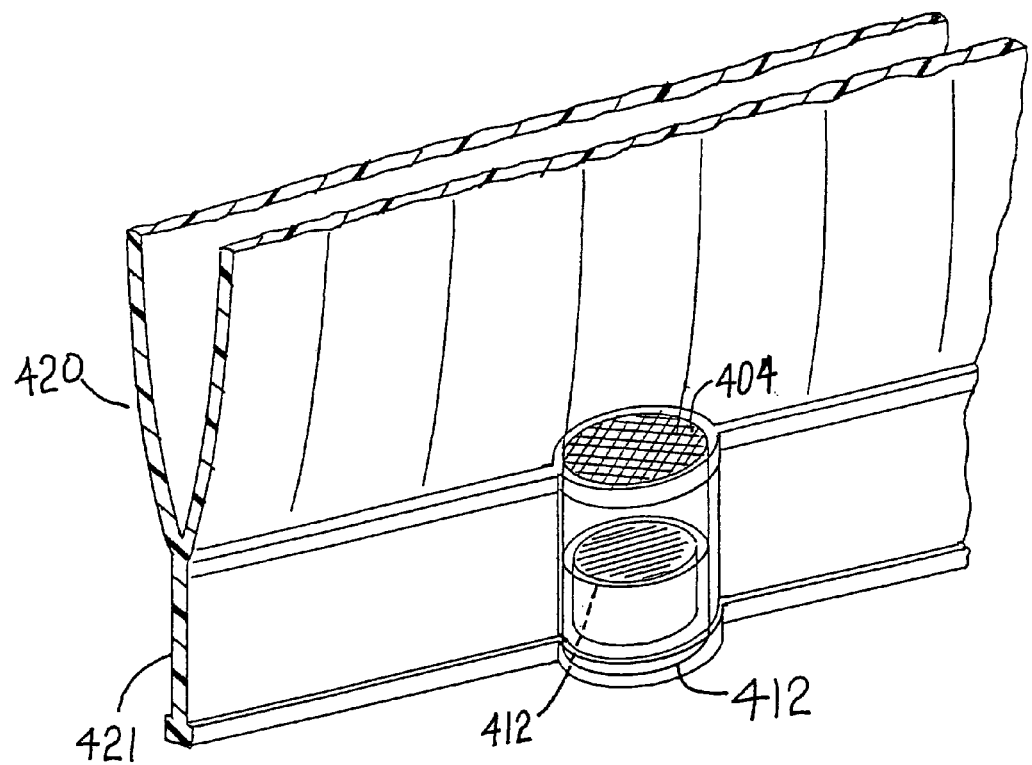
Figure 5A:
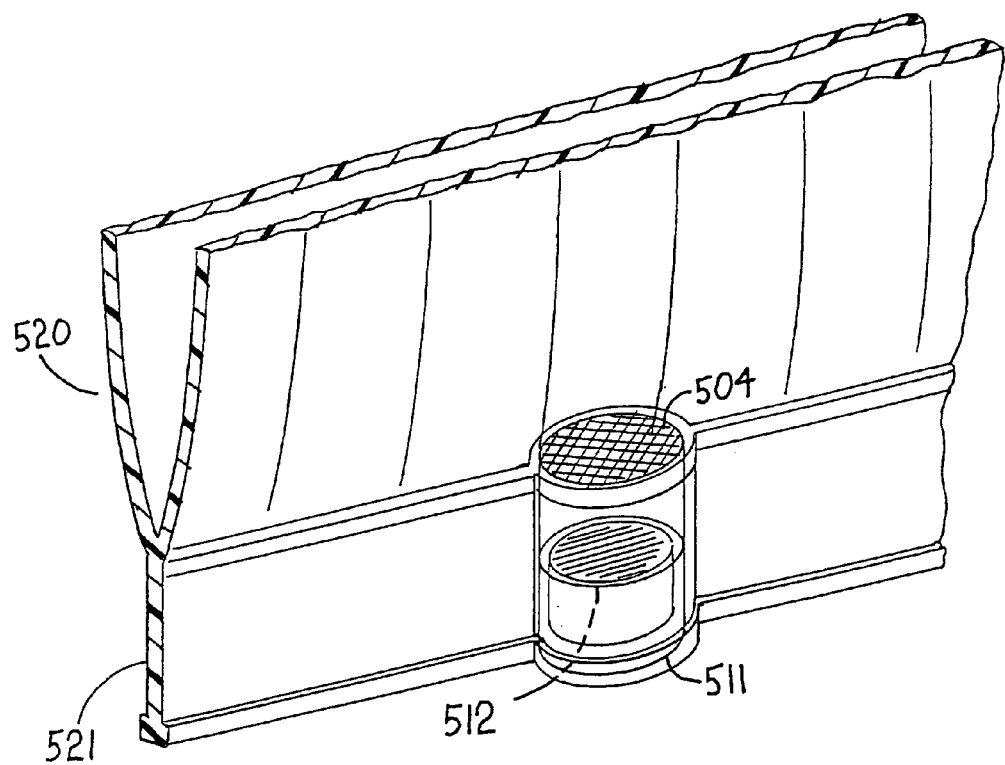

It is certified that error appears in the above-identified patent and that said Letters Patent is hereby corrected as shown below:

Delete Figs. 4a and 5a. as shown on attached pages.

Column 21, Line 5, Claim 13, "barrier fonning" should read -- barrier forming --

Column 21, Lines 9-10, Claim 13, "fluid communication" should read -- fluid communication --

Signed and Sealed this

Twelfth Day of January, 2010

David J. Kappos
*Director of the United States Patent and Trademark Office*